(12) United States Patent
Carlson et al.

(10) Patent No.: US 7,207,211 B2
(45) Date of Patent: Apr. 24, 2007

(54) HIGH THROUGHPUT MICROBALANCE AND METHODS OF USING SAME

(75) Inventors: Eric D. Carlson, Cupertino, CA (US); Oleg Kolosov, San Jose, CA (US); Leonid Matsiev, San Jose, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 11/091,607

(22) Filed: Mar. 28, 2005

(65) Prior Publication Data

US 2005/0166679 A1   Aug. 4, 2005

Related U.S. Application Data

(63) Continuation of application No. 10/155,207, filed on May 24, 2002, now Pat. No. 6,928,877.

(51) Int. Cl.
G01N 11/00 (2006.01)

(52) U.S. Cl. .................... 73/54.41; 73/579

(58) Field of Classification Search ............ 73/597
See application file for complete search history.

(56) References Cited

U.S. PATENT DOCUMENTS

| | | | | |
|---|---|---|---|---|
| 2,575,169 | A | * | 11/1951 | Green, Jr. ............... 73/73 |
| 4,103,224 | A | | 7/1978 | Taro et al. |
| 4,294,105 | A | * | 10/1981 | Kelly .................. 73/28.01 |
| 4,312,228 | A | * | 1/1982 | Wohltjen ............... 73/597 |
| 4,535,620 | A | | 8/1985 | Cunnungham |
| 5,201,215 | A | * | 4/1993 | Granstaff et al. ........ 73/54.41 |
| 5,661,233 | A | | 8/1997 | Spates et al. |
| 5,776,359 | A | | 7/1998 | Schultz et al. |
| 5,792,938 | A | | 8/1998 | Gokhfeld |
| 5,855,849 | A | | 1/1999 | Li et al. |
| 5,959,297 | A | | 9/1999 | Weinberg et al. |
| 6,034,775 | A | | 3/2000 | McFarland et al. |
| 6,041,642 | A | | 3/2000 | Duncan |
| 6,126,311 | A | | 10/2000 | Schuh |
| 6,151,123 | A | | 11/2000 | Nielsen |
| 6,157,449 | A | | 12/2000 | Hajduk |
| 6,175,409 | B1 | | 1/2001 | Nielsen et al. |
| 6,182,499 | B1 | | 2/2001 | McFarland et al. |
| 6,327,890 | B1 | | 12/2001 | Galipeau et al. |

(Continued)

FOREIGN PATENT DOCUMENTS

EP   0779510 A2   6/1997

(Continued)

OTHER PUBLICATIONS

U.S. Appl. No. 09/420,334 entitled "Graphics Design of Combinatorial Materials Libraries" (Lacy, et al.) filed Oct. 18, 1999.

(Continued)

*Primary Examiner*—Hezron Williams
*Assistant Examiner*—Rose M. Miller

(57) ABSTRACT

A method and apparatus for measurement of mass of small sample sizes. The method and apparatus is particularly adapted for providing microbalance measurement of solid materials as part of a combinatorial research program. The method and apparatus contemplate monitoring the response of a resonator holding a sample and correlating the response with mass change in the samples.

24 Claims, 9 Drawing Sheets

U.S. PATENT DOCUMENTS

| | | | |
|---|---|---|---|
| 6,336,353 B2 | 1/2002 | Matsiev et al. | |
| 6,371,640 B1 | 4/2002 | Hajduk et al. | |
| 6,393,895 B1 | 5/2002 | Matsiev et al. | |
| 6,401,519 B1 | 6/2002 | McFarland et al. | |
| 6,438,491 B1 * | 8/2002 | Farmer | 701/301 |
| 6,494,079 B1 * | 12/2002 | Matsiev et al. | 73/24.05 |
| 6,507,945 B1 * | 1/2003 | Rust et al. | 717/103 |
| 6,658,429 B2 * | 12/2003 | Dorsett, Jr. | 707/1 |
| 6,664,067 B1 * | 12/2003 | Hajduk et al. | 435/7.1 |
| 6,939,515 B2 * | 9/2005 | Carlson et al. | 422/101 |

FOREIGN PATENT DOCUMENTS

| | | | |
|---|---|---|---|
| JP | 04191639 A | * | 7/1992 |
| WO | WO 96/27125 | * | 9/1996 |
| WO | WO 99/18431 | | 4/1999 |
| WO | WO 00/67086 | | 11/2000 |
| WO | WO 01/77624 | | 10/2001 |
| WO | WO 02/12265 | | 2/2002 |
| WO | PCT/US02/16962 | | 5/2002 |
| WO | WO 03/014732 | | 2/2003 |

OTHER PUBLICATIONS

U.S. Appl. No. 09/550,549 entitled "Automated Process Control And Data Management System And Methods" (Crevier, et al.) filed Apr. 14, 2000.

U.S. Appl. No. 60/311,332, filed Aug. 10, 2001.

Pamphlet, "Hygroscopicity Measurement Apparatus," Puuman, no date.

Hlavay, J. and G.G. Guilbault, "Applications of the Piezoelectric Crystal Detector in Analytical Chemistry", Analytical Chemistry, Nov. 1977, pp. 1890-1898, v. 49, No. 13.

Laine, E., and M. Aarnio, "Device for the Investigation of Humidity-related Behaviours of Materials," Department of Physics, University of Turku, no date.

Surface Acoustic Wave Hygrometer, http://technology.jpl.nasa.gov, accessed Mar. 16, 2002, 2 pages.

Hoenk, Micheal, et al., "Surface Acoustic Wave Hygrometer: Measuring Water Vapor in Earth's Atmosphere," http://mishkin.jpl.nasa.gov, accessed Mar. 16, 2002, 7 pages.

Co-pending U.S. Appl. No. 10/156,222, filed May 24, 2002.

Co-pending U.S. Appl. No. 10/156,329, filed May 24, 2002.

Co-pending U.S. Appl. No. 10/156,295, filed May 24, 2002.

Co-pending U.S. Appl. No. 10/201,181, filed Jul. 23, 2002.

Co-pending U.S. Appl. No. 10/266,047, filed Oct. 7, 2002.

Trolier, Susan et al., "Preparation of Chemically Etched Piezoelectric Resonators for Density Meters and Viscometers", Mat. Res. Bull., vol. 22, pp. 1287-1274 (1987).

Smith, Allan L. et al., "Water sorption isotherms and enthalpies of water sorption by lysozyme using the quartz crystal microbalance/heat conduction calorimeter," Biochimica et Biophysica Acta 1594 (2002), pp. 150-159.

PCT Invitation to Pay Additional Fees with attached Annex to Form PCT/ISA/206—Communication Relating to the Results of the Partial International Search dated Sep. 2, 2003 (PCT/US03/12503).

* cited by examiner

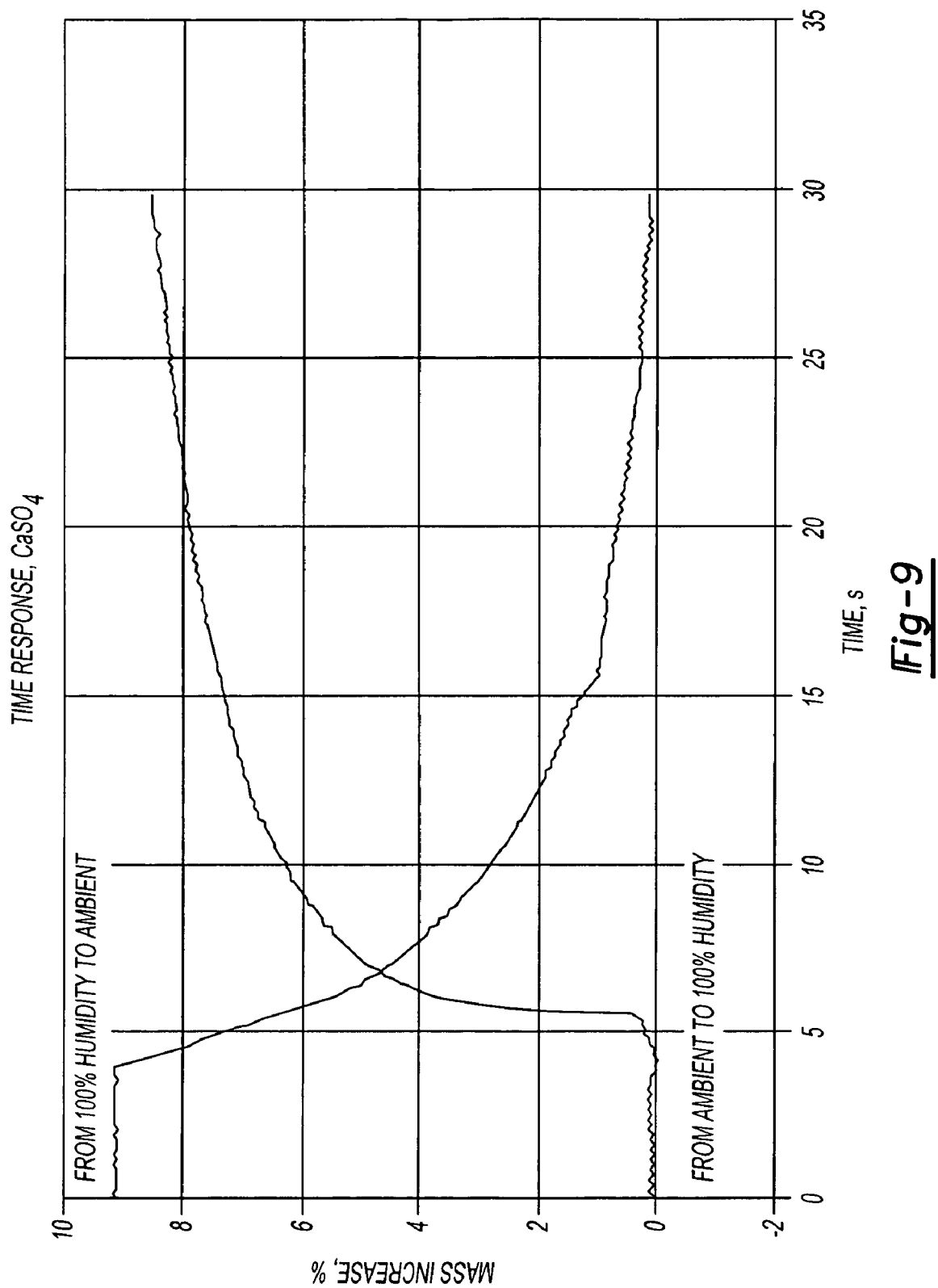

HIGH THROUGHPUT MICROBALANCE AND METHODS OF USING SAME

CLAIM OF PRIORITY

The present invention is a continuation of U.S. application Ser. No. 10/155,207, filed May 24, 2002 now U.S. Pat. No. 6,928,877.

TECHNICAL FIELD

The present invention generally relates to the field of microbalances and methods of using the same. In particular, the invention relates to high throughput microbalances and methods for screening for hygroscopicity.

BACKGROUND OF THE INVENTION

Currently, there is substantial research activity directed toward the discovery and optimization of new materials, including the discovery of new pharmaceuticals. Additionally, substantial research is being directed to formation and processing of such materials. Although the characteristics of these materials including chemistry of the materials, properties exhibited by the materials and the like have been extensively studied, it is often not possible to predict the properties or characteristics that a particular material will exhibit under various conditions or the precise composition and architecture that will result from any particular synthesis scheme. Thus, characterization techniques are an essential part of the discovery process.

Combinatorial chemistry refers generally to methods for synthesizing a collection of chemically diverse materials and/or to methods for rapidly testing or screening this collection of materials for desirable performance characteristics and properties. Combinatorial chemistry approaches have greatly improved the efficiency of discovery of useful materials. For example, material scientists have developed and applied combinatorial chemistry approaches to discover a variety of novel materials, including for example, high temperature superconductors, magnetoresistors, phosphors and catalysts. See, for example, U.S. Pat. No. 5,776,359 (Schultz, et al). In comparison to traditional research, combinatorial research can effectively evaluate much larger numbers of diverse compounds in a much shorter period of time. Although such high-throughput synthesis and screening methodologies are conceptually promising, substantial technical challenges exist for application thereof to specific research and commercial goals.

Recent growth in pre-formulation research (e.g., as may be found for instance in salt selection studies, polymorph studies or the like), in connection with the development of new pharmaceuticals, has driven the need for improved techniques for analyzing properties and characteristics of research candidates. For example, one important consideration in the development and commercialization of pharmaceuticals and other particulated materials is the response of the materials to the environment it is likely to encounter, such as the response of the material to moisture (e.g., humidity). For instance, there is a particular need for the ability to measure small changes in mass occasioned by the uptake or loss of moisture in the material.

SUMMARY OF THE INVENTION

The present invention meets the above need by providing improved microbalance technology (which is operational in rapid serial test format, parallel test or a combination thereof) premised upon the employment of sensitive mechanical resonators, whose resonance performance can be monitored and correlated with mass.

The present invention thus is directed in one preferred aspect to a method for screening at least four fluid samples for moisture content, comprising the steps of (a) providing a plurality of solid samples; (b) placing a first sample onto a mechanical resonator in signaling (e.g., electrical, magnetic, optical, thermal, or other communication) communication with a source of an input signal (and also preferably a signal output detector); (c) coupling the mechanical resonator with measurement hardware (which may be the same as or different from a signal output detector); (d) exposing the samples to moisture while on the mechanical resonator; (e) applying an input signal; (f) monitoring a response of the mechanical resonator to the moisture of the samples thereon with the measurement hardware; and (g) repeating steps (b) through (f) for at least three additional samples. However, it can also readily be adapted for conducting analysis of absolute mass or mass change, such as in response to a change of temperature, (e.g., as for thermogravimetric analysis) or as the result of another change of condition. Further, the concepts herein are particularly suitable for use in a single-channel instrument, wherein a single detector is used for analyzing a single sample in accordance with the teachings herein.

It is possible to operate the present invention in a variety of different modes. For example, without limitation, it is possible that a monitoring step may include monitoring the change in electrical feedback from the resonator while maintaining a constant driving amplitude or vibration amplitude (or combination thereof) at a predetermined frequency.

The monitoring that occurs in step (d) may employ a suitable lock-in amplifier or like hardware for monitoring the change of frequency of the mechanical resonator while maintaining the input signal to the resonator as a constant. It may alternatively employ the monitoring of the change in electrical feedback from the resonator while maintaining a constant frequency.

In a particularly preferred embodiment wherein the input signal is a variable frequency input signal and the monitoring step (d) includes varying the frequency of a variable frequency input signal over a predetermined frequency range to obtain a frequency-dependent resonator response of the mechanical resonator.

The present invention advantageously allows repeating steps to be performed simultaneously for analyzing an array of samples in a parallel format. Yet, as desired, the repeating steps may be performed serially.

In a highly preferred embodiment the method of the present invention is employed as part of a research program for analyzing samples that are pharmaceutical pre-formulation (e.g., salt selection and/or polymorph) candidates. Thus, it is contemplated that in addition to measuring mass one or more additional screens are performed, such as x-ray analysis of the samples.

In one highly preferred embodiment of the present invention there is contemplated a method for screening at least four fluid samples for hygroscopicity, comprising the steps of (a) providing an array of different particulated pharmaceutical polymorph candidate samples; (b) providing a tuning fork resonator having at least two tines with tips and being in electrical communication with a source of an input signal; (c) adhering a quantity of a plurality of samples to at least one of the tines; (d) coupling the tuning fork resonator with measurement hardware; (e) simultaneously, for at least two samples of the array, humidifying the samples while on the tuning fork resonator; (f) simultaneously, for at least two samples of the array, applying a variable frequency input signal; (g) simultaneously, for at least two samples of the array, varying the frequency of a variable frequency input signal over a predetermined frequency range to obtain a frequency-dependent resonator response of the mechanical resonator to the humidification of the samples; and (h) displaying the responses for each of the samples analyzed (either graphically, such as including text, or otherwise), such as by providing n alphanumeric output or readout of a frequency response, or further possibly wherein frequency versus signal is plotted.

As discussed herein, the present invention is also suitable for mass analysis of individual samples, such as by using one or more mechanical resonators. One such method for screening for mass, comprises the steps of: providing a sample; placing the sample onto a region of a mechanical resonator, in which region the oscillation amplitude is relatively high and there is a relatively low stress field, in signaling electrical, magnetic, optical, thermal, or other communication with a source of an input signal, the mechanical resonator being selected from the group consisting of flexural resonators, torsional resonators, or combinations thereof; placing the resonator in signaling electrical, magnetic, optical, thermal, or other communication with a source of an input signal; coupling the mechanical resonator with measurement hardware; applying an input signal for oscillating the resonator at a suitable frequency (e.g., at a frequency of less than about 1 MHz); and monitoring a response of the mechanical resonator to a mass of the sample thereon with the measurement hardware.

Another aspect of the present invention contemplates an apparatus for measuring small quantities of materials, comprising a plurality of resonators, and particularly tuning fork resonators having tines with tips; a holder for each resonator; a readout board; a plurality of elongated members for bridging electrical communication between the resonator and the readout board; and a frame carrying at least the resonators, holders and elongated members. The apparatus is preferably adapted for attachment to a robot arm for facilitating automation of the operation of the apparatus. The apparatus of may further comprise other components, such as a sample work surface having a recess therein for receiving a sample, a host computer, and a power source (e.g., for providing a variable frequency input signal to the resonators).

The advantages of the present invention are numerous and are mentioned throughout this written description or are otherwise gleaned therefrom. In one particularly preferred aspect, the present invention is useful for and is used for mass measurements of soft, thick, non-uniform layers or irregularly shaped samples. The ability to use the present invention for gravimetric measurements also renders this technology suitable for inclusion in an analytic program for any of a number of different fields such as biotechnology, pharmaceutical research, gel and powder technology.

The present invention is also useful for and is used for small quantity measurements, with some samples being less than about 100 micrograms and more preferably less than about 50 micrograms. Further, for certain of the resonators herein (e.g., tuning fork resonators) Q-factor does not decrease by more than about 1–3%, so relative change of a sample mass is accurately measured by resonator frequency change. Transient response of a resonator to a sample mass change can be estimated as about two to about three times the Q-factor, divided by resonant frequency, that allows for performing measurements in less than one minute (e.g., less than about 5 seconds) and for real-time mass tracking.

BRIEF DESCRIPTION OF THE DRAWINGS

FIG. 9 is an illustrative sample transient response plot in accordance with the present invention.

DETAILED DESCRIPTION OF THE PREFERRED EMBODIMENTS

Figure 1:
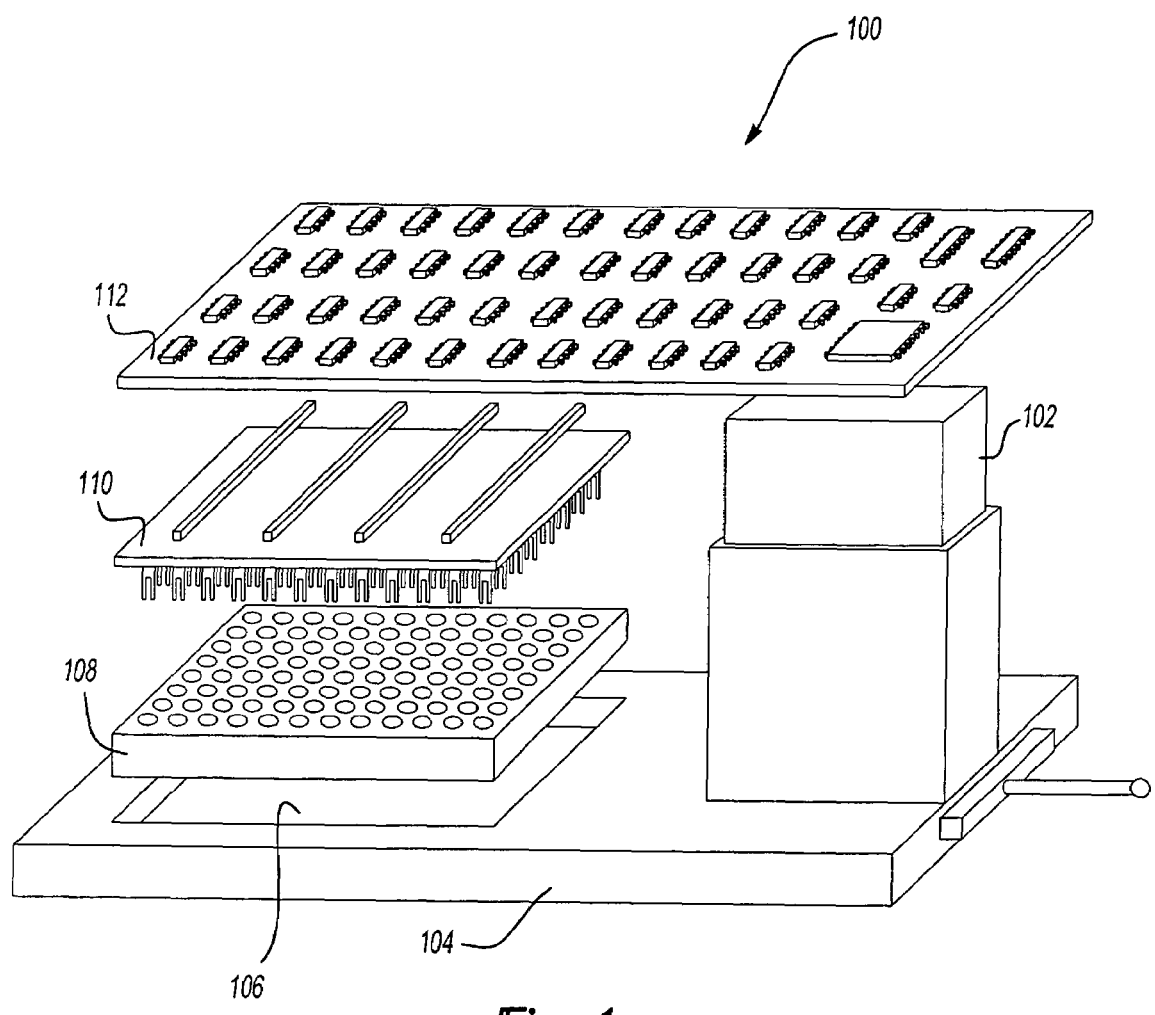
FIG. 1 shows an exploded perspective view of one preferred system of the present invention.

As will be appreciated from the description herein, the present invention is directed primarily for measuring microscopic amounts of materials. One highly preferred use of the present invention is the measurement of moisture uptake or loss of a solid material, and more specifically a finely particulated solid material. Even more specifically, a preferred use of the present invention is for the measurement of hygroscopicity of pharmaceutical compounds, in the course of doing salt selection studies, polymorph studies, or the like. Accordingly, though illustrated herein in connection with such highly preferred use as a hygroscopicity measure, the present invention has a wide variety of uses and the invention is not intended to limit the invention herein disclosed.

The samples for which the present invention is particularly useful for analyzing includes any solid material capable of moisture uptake or loss, by absorption, desorption, adsorbtion, capillary uptake of the like. However, it may be also adapted for measurement of fluid deposition onto a bare resonator in accordance with the present invention. The invention may also be readily employed for thermogravimetric analysis, by which a sample mass is monitored over time and under a predetermined temperature condition. It may also be employed for any application requiring high sensitivity detection of a mass change.

Preferred materials that are analyzed herein are particulated materials, and especially finely divided particulates or powders. Thus, the present invention is particularly employed for measurement of mass changes, such as from moisture changed, of small molecules, ceramics, polymers, metals, carbon, composites or the like. A highly preferred application of the present invention is for the measurement of mass (e.g. from moisture) changes of pharmaceutical compounds, and even more particularly the hygroscopicity of powdered pharmaceuticals. An even more preferred application is for the rapid throughput measurement of hygroscopicity of salt selection candidate samples, polymorph candidate samples, or both as part of a pharmaceutical research program. It will be appreciated that the term "polymorph" as used herein is intended to cover not only polymorphs, but also solvates (e.g., forms containing solvent), or water and desolvated solvates and amorphous forms of a substance. In this regard, the present invention is believed to find application and utility as an analytical instrument that may be used in combination with the subject matter that is disclosed in commonly-owned, copending U.S. application Ser. No. 10/156,222, now published as U.S. 2003/0124028 entitled "Apparatuses and Methods for Creating and Testing Pre-Formulations and Systems" and filed on this dated, the subject matter of which is hereby expressly incorporated by reference herein for all purposes.

The present invention is particularly applicable to the measurement of mass change, such as that which might be observed by moisture uptake or loss of particulated materials. The present invention is not, however, limited to only particulated materials and may be used for measuring mass change, such as fluid uptake or loss in thin films, monoliths, rods, plates, discs, wires, or any other suitable solid form. When employed for measuring particulated materials the average particle size can be on the nano-scale (e.g., nano-particles), but more typically will have an average diameter ranging from about 0.01 um to about 1000 um, more typically from about 0.1 um to about 100 um, even more typically less than about 75 um, and still more preferably, less than about 50 um (with particles sizes even less than about 5 um possible). In this regard, the particulated materials may be prepared for analysis in any suitable manner, such as by suitable crushing, milling, pulverizing or other suitable micronizing step, with optional mixing, packing or the like.

The samples that are analyzed in accordance with the present invention may be homogeneous (e.g., pure compound) or they may be heterogeneous (e.g., they may be provided with a binder, adhesive, matrix or carrier material). It is also possible that the samples under consideration may be employed with a suitable performance enhancing agent, such as a preservative, filler, lubricant, surfactant, flavorant, disintegrating agent, granulating agent, or a combination thereof (either as a homogeneous or heterogeneous material).

The present invention thus can be employed to measure the effects on hygroscopicity of a pharmaceutical compound candidate under variable conditions and processing parameters, including but not limited to humidity level humidity pH, humidity contaminants, crushing, packing, milling, mixing, or the like.

The present invention is not limited to applications in the pharmaceutical fields, but may be also used in a method to measure absolute mass, the moisture absorption or desorption (or other factors correlated with mass or mass change) of any of a number of different materials, such as solid or semi-solid materials such as existing or novel polymers, polymer blends, surfactants, oligomers, and the like. Other applications are discussed elsewhere herein.

The present invention is particularly attractive because of its ability to yield reproducible and reliable measurement of mass in microscopic quantities or resulting from the measurement of small sample quantities. For example, typical sample sizes can range from about 0.1 microgram to about 1 gram, more typically from about 1 microgram to about 100 milligrams, even more typically less than about 75 micrograms, and still more preferably less than about 40 micrograms.

It should also be appreciated that even though the present invention is disclosed, in one preferred aspect, as a screening technique as part of a combinatorial research program, it has other applications, including but not limited to the provision of a microbalance for measuring small quantities of individual or a plurality of bulk materials in a commercial (rather than a research) environment, such as an on-line process or inventory quality control measure employing only one or a plurality of resonators in accordance with the teachings herein.

In a combinatorial approach for identifying or optimizing materials, properties, conditions or reactions, a large compositional space (e.g., of variable structures or ratios of components) or a large reaction condition space (e.g., of temperature, pressure, humidity or reaction time) may be rapidly explored by preparing libraries of 2 or more, 4 or more, 16 or more, 48 or more, or even 96 or more samples (e.g., using an art-disclosed techniques, such as is set forth in U.S. Pat. No. 5,776,359 (Schultz, et al)), and then rapidly screening such libraries. The libraries may be synthesized or screened on a common substrate or two or more different substrates.

Samples within a library may differ, including with regard to chemical structure, processing or synthesis history, mixtures of interacting components, post-synthesis treatment, purity, etc. In a particularly preferred embodiment, the samples are spatially separated, such that members of the library of samples are separately addressable. All samples in a library may be the same or different relative to each other. When process conditions are to be evaluated, for example, the libraries may contain only one type of sample. The use of reference standards, controls or calibration standards may also be performed, though it is not necessary. The samples of a library may be previously characterized, uncharacterized or a combination thereof, so that property information about the samples may not be known before screening.

Combinatorial approaches for screening a library can include an initial, primary screening, in which material samples are rapidly evaluated to provide valuable preliminary data and, optimally, to identify several "hits" —particular candidate samples having characteristics that meet or exceed certain predetermined metrics (e.g., performance characteristics, desirable properties, unexpected and/or unusual properties, etc.).

It may be advantageous to screen more focused libraries (e.g., libraries focused on a smaller range of compositional gradients, or libraries comprising compounds having incrementally different structural variations relative to those of the identified hits) and additionally or alternatively, subject the initial hits to variations in process conditions. Once one or more hits have been satisfactorily identified based on the primary screening, libraries focused around the primary-screen hits might be further evaluated with a secondary screen—a screen designed to provide (and typically verified, based on known materials, to provide) chemical composition, sample content or process conditions that relate with a greater degree of confidence to commercially-important processes and conditions than those applied in the primary screen. Particular samples that surpass the predetermined metrics for the secondary screen may then be considered to be "leads." If desired, identified lead samples may be subsequently prepared in bulk scale or otherwise developed for commercial applications through traditional bench-scale and/or pilot scale experiments.

In general, combinatorial research can be performed in a high throughput manner by art-disclosed rapid-serial, parallel techniques or a combination of these techniques. In a rapid-serial approach, a plurality of samples are consecutively addressed in relation to each other (i.e., for serial analysis of the samples). In a parallel approach, two or more samples are addressed simultaneously. It is also possible that two or more samples can be simultaneously addressed followed by the advancing to a new additional sample on a rapid serial basis. The present invention may be used in connection with any or all of the above high-throughput formats.

As used herein, the phrase "mechanical resonator" is intended to include mechanical piezoelectric resonators, and particularly quartz resonators. A highly preferred mechanical resonator for employment herein is a flexural resonator such as a tuning fork resonator, which offers an advantage of being able to be oscillated at a relatively low frequency range (e.g., in a preferred embodiment, it is operated in the range of less than about 1 MHz, more preferably up to about 500 kHz, still more preferably about 1 to about 100 kHz, (e.g., about 32 kHz)).

Additionally, as for highly preferred flexural resonators, they will preferably flex primarily at the base of their respective tines. They can thus be very sensitive to mass mounted at the end of the tine. Thus, it is preferred that there will generally be no resonator structural flex at the location where the sample is mounted. Therefore, results from a preferred method generally are not generally sensitive to how the sample is mounted.

In one embodiment, for analysis of plural samples herein, the sample materials are provided for analysis on a common supporting structure, such as a suitable substrate. The substrate can be a structure having a rigid or semi-rigid surface on which or into which the library of samples can be formed, mounted, deposited or otherwise positioned. Preferably the substrates will be a structure adapted for receiving at least 4 different samples in spaced relation to each other, such as micro-titre plate, a block adapted for holding sample vials or the like. The substrate can be of any suitable material, and preferably includes materials that are inert with respect to the samples of interest, or otherwise will not materially affect the mechanical or physical characteristics of one sample in an array relative to another. Non-conventional substrate-based sample containers, such as relatively flat surfaces having surface-modified regions (e.g., selectively wettable regions) can also be employed. The overall size and/or shape of the substrate is not limiting to the invention. The size and shape can be chosen, however, to be compatible with commercial availability, existing fabrication techniques, and/or with known or later-developed automation techniques, including automated sampling and automated substrate-handling devices. The substrate is also preferably sized to be portable by humans, thereby permitting analysis, either on or off of the substrate, in accordance with the present invention and one or more additional different screens, the performance of which is also contemplated herein. The substrate can be thermally insulated, particularly for high-temperature and/or low-temperature applications.

Because the present invention requires relatively small sample sizes, it provides a useful vehicle for analysis, particularly because there will commonly remain an excess sample materials on the substrate, after analysis herein, available for other additional screening techniques.

Referring to FIG. 1, there is illustrated one preferred system 100 of the present invention. The system 100 includes a frame 102 adapted for assembly of a sample work surface 104 (e.g., a flat surface, or one having a recess 106 or other suitable structure for conforming with or otherwise holding a sample container 108 or a sample itself) with measurement hardware of the present invention. The work surface 104 may substitute therefore or include in combination therewith a suitable site for receiving an environmental condition chamber (as described herein).

It should be appreciated that the discussion herein, in conformance with the drawings is specifically addressed to a system adapted for simultaneous measurements of a plurality of samples. However, the invention is not intended to be limited thereby, and it will be appreciated that the present invention also covers the use of individual measuring elements by themselves, whether in rapid serial format or not. Thus, the references to plural components are for convenience and singular components may be used in isolation as well.

The hardware of the system 100 preferably includes a plurality of resonators in a resonator array 110, each resonator optionally adapted for receiving a sample, suitable connections to a source for oscillating the resonators, and a device for measuring the responses of the resonators. One preferred system additionally includes one or both of the source for oscillating the resonators and a suitable host computer. Preferably, suitable readout electronics are employed, e.g., including a readout board 112, for interfacing between the computer and the resonator.

As will be seen, the present invention, though it can be configured in a suitable hard-wired configuration, preferably takes advantage of the ability to use printed circuit board technology. In this manner, the present invention advantageously provides a desk-top instrument (e.g. having a real estate footprint smaller than about 2.5 m$^2$, and more preferably less than about 1.5 m$^2$), which is capable of analyzing many samples on a rapid throughput basis.

The entire system 100 may be assembled with a common frame or a plurality of different frames. Further, it is possible that the system 100 may include one or more additional components that are not shown, such as an exhaust hood, an automated sample handler, a robot arm onto which the resonators or the samples are placed for automated translation, or the like. The system or components thereof may be partially or fully enclosed for creating a desired environment as well.

Figure 3A:
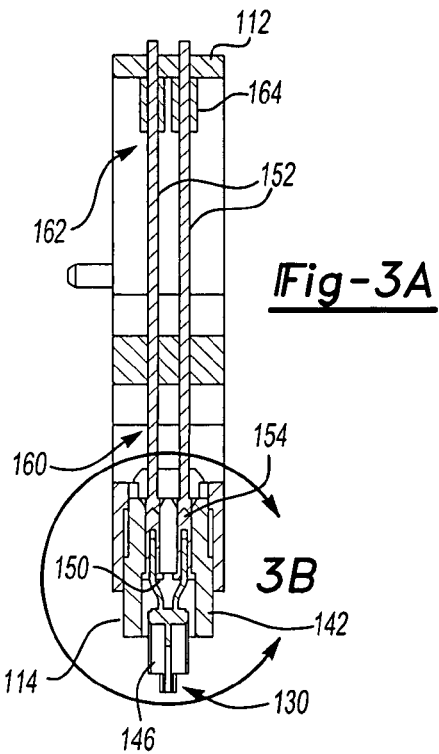
FIGS. 3A and 3B are sectional views depicting a resonator element of the present invention.
Figure 3B:
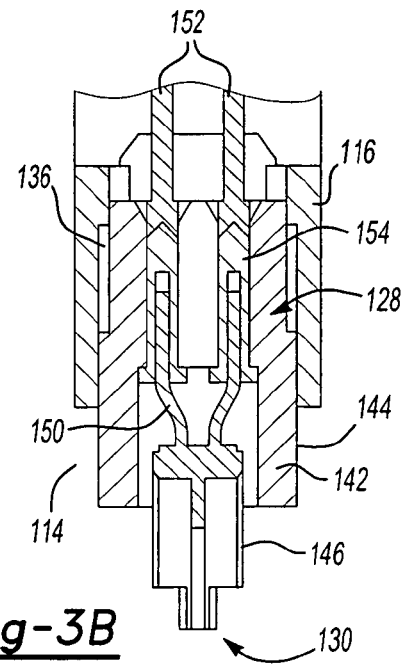
Figure 3C:
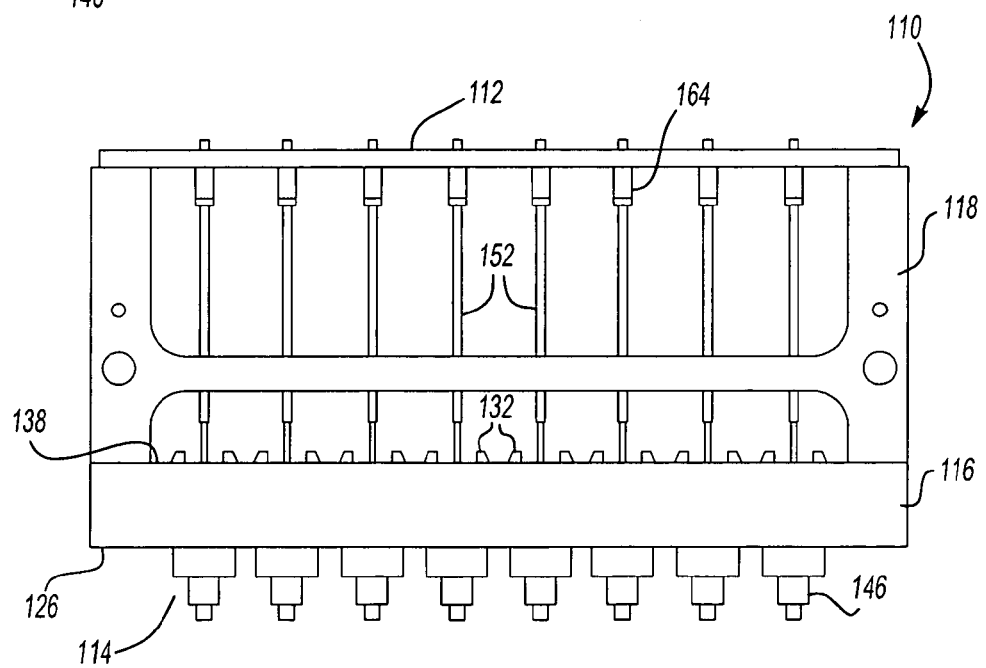
FIGS. 3C and 3D are side and bottom views respectively of a resonator array of the present invention.
Figure 3D:
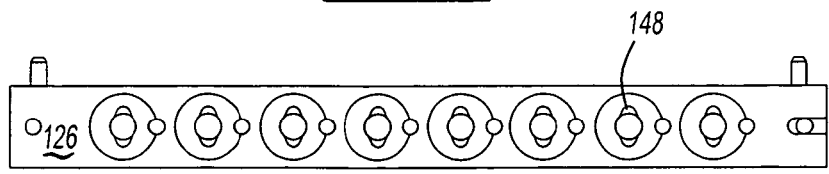
Figure 4A:
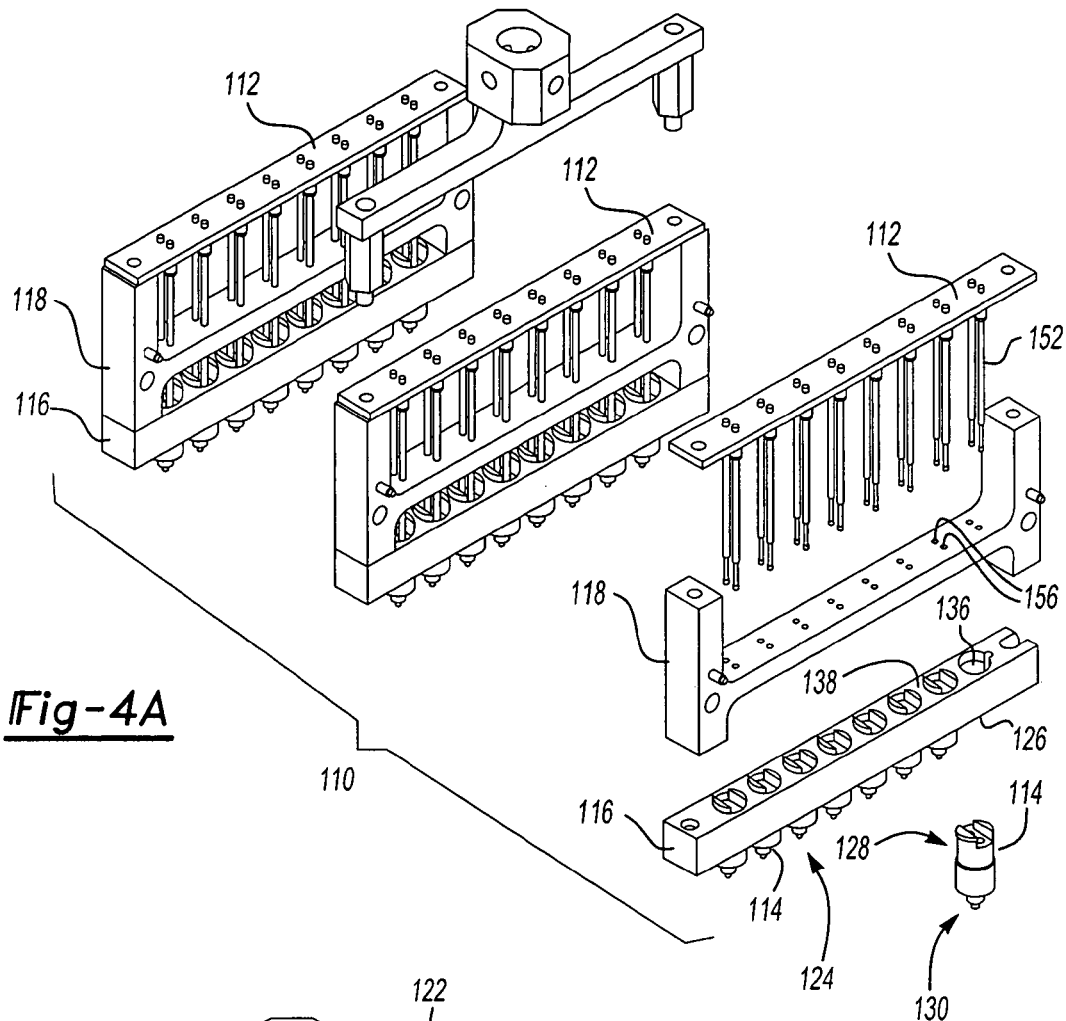
FIG. 4A shows an exploded perspective view of one preferred resonator assembly of the present invention.
Figure 4B:
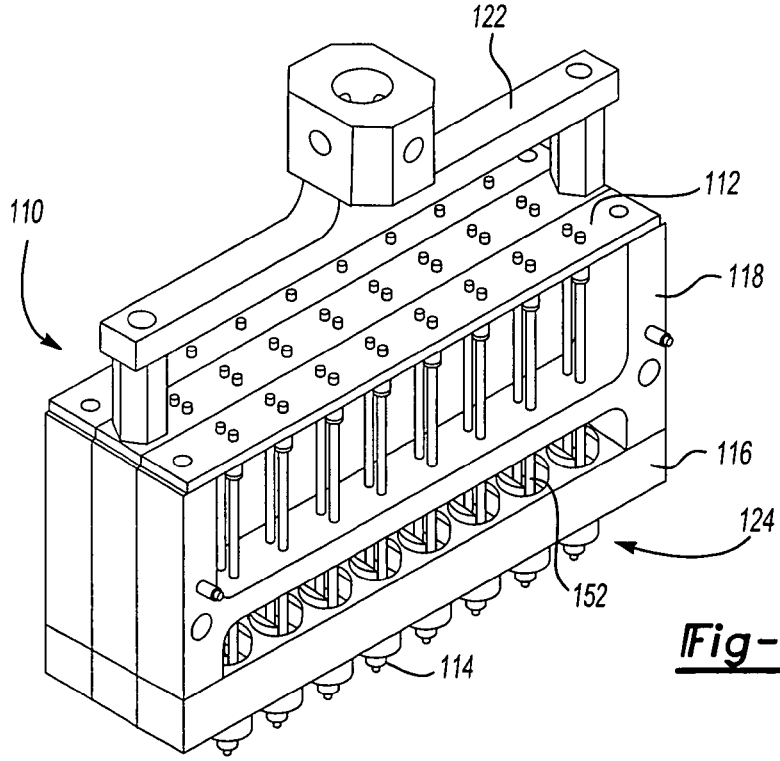
FIG. 4B shows a perspective view of the preferred resonator assembly of FIG. 4A.

Turning to FIGS. 2A–4B, there is illustrated an example of one preferred resonator array 110 in accordance with the present invention. Shown particularly in FIG. 4C, the resonator array 110 includes a plurality of resonator elements 114 assembled onto a common carrier structure, such as an element holder 116. The carrier may be attached to a frame 118 (e.g., with a plurality of intermediate connecting probes), or directly to the readout board 112. As depicted in FIGS. 4a and 4b, a plurality of element holders 116 can be assembled to form an array of a desired size. Optionally, a single holder may be employed. There may also be employed a suitable mounting bracket 122, which is attached to the resonator array 110 and can also be translated to a suitable structure or device (e.g., a suitable robot arm, like that available from Tecan Systems (formerly Cavro Scientific Instruments)(San Jose, Calif.)) for locating the position of the resonator array 110 relative to samples for measurement.

Resonator elements 114 are suitably positioned on their respective element holders 116. In one preferred embodiment, the elements 114 include a resonator 122 that has an exposed portion 124, which projects away from a base surface 126 of the element holders 116. The element holders may partially or fully surround the elements as desired. The elements may be permanently affixed to the holder or affixed by temporary means or other means for permitting removability. For example, the holder and elements may be threaded for fastening attachment, configured for snap fit attachment (e.g., as described herein), welded, adhered, or otherwise attached. It should be appreciated that resonator elements thus may be fabricated from suitable materials or in a suitable manner such that may be employed for single-use only applications and thus be disposable.

Figure 2A:
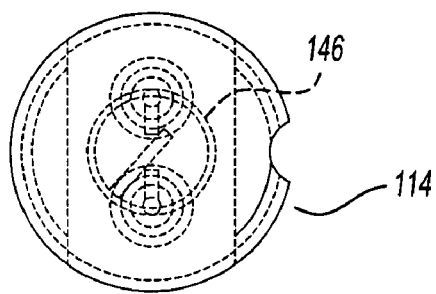
FIG. 2A shows a bottom plan view of an illustrative resonator element of the present invention.
Figure 2B:
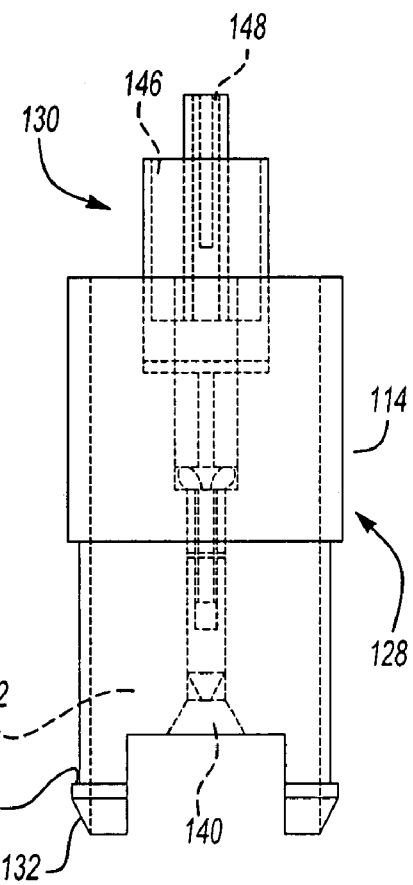
FIG. 2B is a sectional view of the element of FIG. 2A.
Figure 2C:
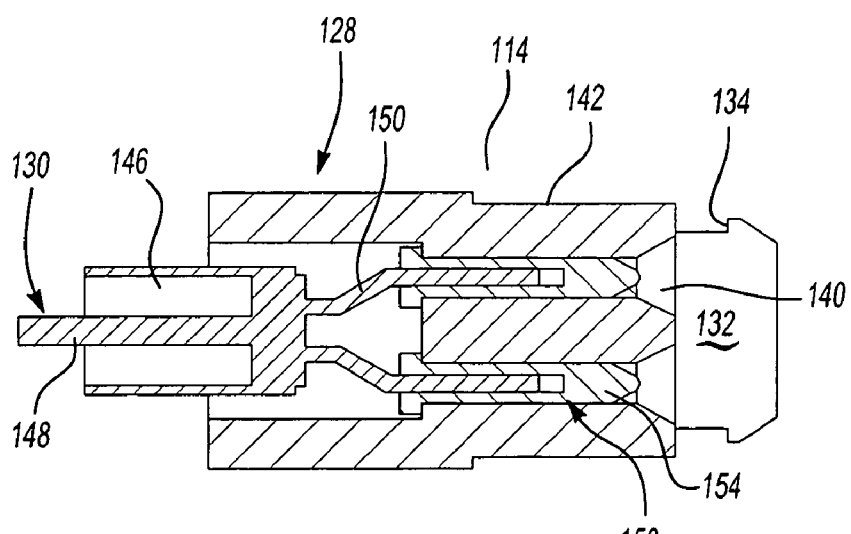
FIG. 2C is another sectional view of the element of FIG. 2A.

FIGS. 2A–2C illustrate one possible structure for an element 114. The element has a mounting portion 128 and a sensor portion 130, seen in FIGS. 2B and 2C. The mounting portion 128 is illustrated as substantially surrounding the sensor portion 130. However, the sensor portion 130 may otherwise be held in place relative to the mounting portion (e.g., attached to an external surface of the mounting portion). The mounting portion preferably is configured for ease of placement, either on a permanent or a temporary basis, in one of the element holders 116 (e.g., as seen in FIG. 3C). For example, an exterior surface of the mounting portion may be adapted for threadingly engaging an interior wall surface of the holder 116. The mounting portion may penetrate through some or all of the holder 116. Alternatively, it may be affixed to an external surface of the holder 116. In one particularly preferred embodiment, the mounting portion 128 is configured with opposing squeeze tabs 132, having detents 134 adapted for penetrating through a through-passage 136 (shown best in FIG. 4A) of the holder and lockingly engaging a surface 138 opposite the base surface 126. The tabs preferably are, but need not be, such that they can be subsequently removed from the holder 116.

The mounting portion 128 preferably includes a suitable mounting hole 140 for permitting access to the sensor portion from the surface 138. Any suitable shape for a body 142 may be employed for defining the mounting portion. Preferably, the body 142 will have an outer wall surface 144 (with a continuous surface as in FIG. 3B or including cut-outs), at least a portion of which substantially conforms in dimension and geometry with at least a portion of the interior wall surface that defines the aperture 136 of the holder 116. In this manner, the elements preferably can be and preferably are maintained in stable alignment upon assembly. By way of example, the body 142 depicted in the drawings includes at least one cylindrical portion, and more preferably a plurality of cylindrical portions of different diameters. Other shapes may be employed as desired, including triangular, rectangular or other polygonal prism shapes, cones, or the like. A corresponding complementary shape preferably would define the interior wall surface. Additionally or alternatively, one or more seals, gaskets, shims, adapters or the like could be employed for permitting attachment of an element to the holder.

Optionally, either the mounting portion 128, the sensor portion 130 or both includes a suitable baffle, sheath or other like wall structure 146 that serves to shield some or all of a resonator 148, to help locate the resonator relative to a sample, or both. The wall structure 146 may entirely surround the resonator 148 (as shown in FIGS. 2A–2C) or partially surround it. It may be integrally formed on the resonator or attached thereto.

Referring more specifically to FIG. 2C, in one preferred embodiment, there is shown a resonator 148 having leads 150 that are secured within the mounting holes 140 of the mounting portion. Preferably the leads are of a relatively fine diameter (e.g. on the order of about 0.015 to about 0.025" (0.35 to about 0.65 mm)). Though other configurations may be suitably employed the arms or electrodes preferably are adapted for communication with a plunger 152 (see FIG. 3A). Thus, in one illustrative embodiment, a receptacle 154 at least partially surrounds the leads 150, and is press fit or otherwise secured within the mounting holes 140 of the mounting portion. The receptacle may be any suitable receptacle, and in one embodiment is a wrap post receptacle, and more particularly includes a shank portion 158 (that may be cut to the desired dimensioned), and preferably includes a shell portion and an electrical contact portion. The electrical contact portion, the shell or both may be a gold, or tin/lead conductor or the like plated over nickel (optionally copper beryllium contacts may be plated). Preferably the electrical contact portion is press fit within the shell and is adapted for receiving the lead 150. An example of a particularly preferred receptacle is available from Mill-Max Mfg. Corp. under the product designation 0066-3. Of course, others may be selected as well.

Referring again to FIG. 2C, the shank portion 158 of the receptacle 154 is preferably adapted for receiving or otherwise contacting the plunger 152. The shape of the shank portion cross section may vary. For instance, it can be circular, polygonal (e.g., square) or otherwise. Optionally, the plunger may be attached to the receptacle, such as by a suitable solder, conductive adhesive, joint fitting or the like.

In FIGS. 3A and 3B there is illustrated one possible approach to connecting the resonator elements to a readout board. In this embodiment, as discussed previously, plungers 152 are employed for establishing communication between individual resonators and the readout board 112. The plungers 152 are arranged in generally parallel alignment with each other, although they may be disposed otherwise. The frame 118 provides a stand-off for supporting or bridging structure as between the holder 116 and the readout board 112. In this regard, it may be adapted for passage there through of the plungers, such as via apertures 156 (FIG. 4A) in the frame 118.

The plunger 152 is adapted for providing bridging communication between a resonator element and the circuitry for oscillating or measuring the response of the resonator. The plunger 152 includes a first end portion 160 that adjoins the receptacle 154 and a second end portion 162 that adjoins the readout board 112.

The plunger may be a rigid member, or it may be rigid but also contain a resilient portion, such as a spring-loaded portion. For example, the plunger may include a spring-biased post translatable relative to a barrel. According to the latter, the presence of a spring permits the plunger to be compressed upon itself during loading and unloading assembly operations or otherwise during operation of the apparatus of the present invention. It also allows for flexibility in the dimensional tolerances of other components of the assembly.

The end portions of the plungers may terminate in any suitable tip structure, such as a pointed tip, a rounded tip, a flat tip, a concave shape, a convex shape, serrated, or the like. The components of the plunger may be made of any suitable material, such as, without limitation, a beryllium copper (palladium, rhodium plated or otherwise plated) for a post; a nickel silver, gold plated material, or a work-hardened phosphor bronze plated over hard nickel for the barrel; and a stainless steel, gold plated, a beryllium copper or even a music wire for the spring. Other materials are also possible as will be appreciated and the above is not intended as limiting. Examples of preferred commercially available plungers are available under the trademark Pogo®, for example IDI Pogo SC0J-3.2.

The plungers are connected to the readout board in any suitable manner, and preferably by the use of one or more suitable receptacles 164 (See FIGS. 3B and 3C). In one embodiment, the receptacles are configured for and are press fit into apertures in the readout board. However, they may be secured in any suitable manner. The receptacle may be any suitable receptacle, and in one embodiment includes a shell portion and an electrical contact portion at least partially enclosed by the shell portion. The electrical contact portion, the shell or both may be a gold,.or tin/lead conductor or the like plated over nickel (optionally copper beryllium contacts may be plated). An example of one preferred receptacle is that such as is commercially available from Mill-Max Mfg. Corp. under the product designation 0501-015153014.

Of course, it is also possible that the resonator leads are connected directly to a signal source, in the absence of a plunger. Moreover, structure other than a plunger may also be employed for performing the plunger function, or where it is otherwise desirable to space the resonators from any readout electronics, such as the readout board 112 depicted in FIG. 3c.

FIGS. 4A and 4B illustrate one possible configuration for a resonator array 110 of the present invention. In this embodiment a plurality of holders 116, frames 118 and readout boards 112 are separately fabricated and assembled together with the plungers and receptacles, either before or after securing the resonator elements in place. In the embodiment illustrated a plurality of holders of a 1×N configuration (N is an integer 1 or greater and represents sites for a resonator) and assembled together with at least one common carrying bracket 122. The carrying bracket 122 preferably is adapted for permanent or temporary attachment to the system frame 102, a robot arm or some other structure whose position relative to one sample or an array of samples can be controlled.

As mentioned, the holders 116 shown are 1×N holders (e.g., 1×1, 1×2, 1×4, 1×8 or the like), but may be an M×N format, where both M and N are integers one or greater. Moreover, a resulting array may include 2 or more resonator sites, 4 or more, 8 or more, 16 or more, 24 or more, 48 or more or even 96 or more individual resonator sites, which as desired may be preferably individually addressed, or addressed in groups of two or more sites.

Preferred resonators of the present invention are selected from the group consisting of flexural resonators, torsional resonators, or combinations thereof. A highly preferred embodiment of the present invention contemplates employing a tuning fork as a resonator for the resonator elements. Preferably a two tine tuning fork is employed as the resonator. However, the method and system of the present invention can use any type of tuning fork resonator, such as a trident (three-prong) tuning fork or tuning forks of different sizes, without departing from the spirit and scope of the invention. Examples of preferred commercially available tuning forks include those available from Seiko-Epson, under the designation C-001R 32.768K-A, or from Citizen Corporation, under part number CFS308-32.768KDZFB.

As indicated, the present invention is not intended to be limited to tuning fork resonators. Other types of resonators can be used, such as thickness shear mode resonators, tridents, cantilevers, torsion bars, bimorphs, membrane resonators, length extension resonators, torsion resonators, unimorphs, or various surface acoustic wave devices, or combinations thereof. More preferred resonators are selected from tuning forks (e.g., two-tine, tridents or the like), cantilevers, bimorphs, or unimorphs. A plurality of the same-type or different types of resonators can be used in combination. For example, a low frequency resonator may be employed with a high frequency resonator.

It will be appreciated that a tuning fork herein is an excellent candidate for providing a microbalance for measuring small amounts of mass change. Without intending to be bound by theory, because the resonance frequency depends on the effective mass of a tine, any change in the mass on the tine will change the resonance response of the tuning fork. An increase in the mass associated with the tuning fork will therefore reduce the resonance frequency of the tuning fork in a measurable way.

Exemplary technology that can be adapted for use in the present invention includes that disclosed, for example, in U.S. Pat. No. 6,336,353 (Matsiev, et al.) ("Method and apparatus for characterizing materials by using a mechanical resonator"); and U.S. Pat. No. 6,182,499 (McFarland, et al.) ("Systems and methods for characterization of materials and combinatorial libraries with mechanical oscillators"); and U.S. patent application Ser. No. 09/723,838 now granted as U.S. Pat. No. 6,401,519, Ser. No. 09/800,829 now granted as U.S. Pat. No. 6,494,079, and Ser. No. 09/133,171 now granted as U.S. Pat. No. 6,393,895, hereby expressly incorporated by reference for all purposes.

The resonator optionally may be coated with a material to change the performance characteristics of the resonator. For example, the material can be a coating, such as to protect the resonator from corrosion or other factors potentially affecting resonator performance. Alternatively, it may be a specialized "functionalization" coating that changes the resonator's response if a selected substance is present in the composition being tested by the resonator. For example, adding a hydrophobic or hydrophilic functionality to the tuning fork tine allows the tine to attract or repel selected substances in the medium being analyzed, changing the mass or effective mass of the tuning fork and thereby changing its resonance frequency.

The resonators can also be functionalized with a polymer layer or other selective absorbing layer to detect the presence of specific molecules in a vapor. The coating or functionality can be applied onto the resonator using any known method, such as spraying or dipping. Further, the specific material selected for the coating or functionality will depend on the specific application in which the tuning fork resonator is to be used. J. Hlavay and G. G. Guilbault described various coating and functionalization methods and materials to adapt piezoelectric crystal detectors for specific applications in "Applications of the Piezoelectric Crystal Detector in Analytical Chemistry," Analytical Chemistry, Vol. 49, No. 13, November 1977, p. 1890, incorporated herein by reference.

A single tuning fork resonator may be coated or functionalized. Alternatively, multiple resonators having the same or a different structure but different coatings and/or functionalities can be incorporated into one sensor. For example, a plurality of tuning fork resonators may have the same structure but have different functionalities, each functionality designed to, for example, bond with a different target molecule. When the sensor is used in such an application, one tuning fork resonator can, for example, be functionalized with a material designed to bond with a first substance while another resonator can be functionalized with a material designed to bond with second substance. The presence of either one of these substances in the sample composition being tested will cause the corresponding tuning fork resonator to change its resonance frequency.

The resonators of the present invention may include a suitable structure for receiving sample, such as a recessed holder or the like. More preferably, however, the samples are held on a resonator with a suitable adhesive, such as a pressure sensitive adhesive. Especially for hygroscopicity measurements, preferably the adhesive is a generally hydrophobic adhesive, such as a silicone adhesive. Suitable silicone adhesives are available from a number of different commercial sources, such as General Electric, The Dow Chemical Company or others. In a highly preferred embodiment, where the resonator is a tuning fork, the adhesive (and the sample in turn) is provided on a tip of the tuning fork or in another low or substantially zero stress region, particularly a region where amplitude of oscillations is high, but the stress field is low. Thus, typically, the sample will be placed on a resonator by contacting the resonator with sample and optionally removing excess sample, such as by shaking, a pulse or flow of a gas, or otherwise.

It may be desirable to tailor the performance characteristics of any adhesive that is employed in order to optimize sample analysis for a particular sample. This may be accomplished in any suitable manner, such as by applying the adhesive to the resonator and then suitably curing (e.g., thermally, by radiation or otherwise) the adhesive for a time sufficient for crosslinking a portion of the adhesive, or performing some other treatment step for lowering the tack of the adhesive or for eliminating potential sources of measurement error as a result of the adhesive.

In one embodiment, as with U.S. Pat. No. 6,336,353 (Matsiev, et al.) and U.S. Pat. No. 6,182,499 (McFarland, et al.), the systems of the present invention may employ a mechanical resonator in signaling communicating with suitable measurement hardware, such as a network analyzer, lock-in amplifier, self oscillatory circuit with resonator in a feed-back loop and a frequency counter. As with other measurement hardware herein, the analyzer is preferably adapted for monitoring the change of frequency of the mechanical resonator while maintaining the input signal to the resonator as a constant. Alternatively, it is adapted for monitoring the change in electrical feedback from the resonator while maintaining a constant frequency.

In one highly preferred embodiment, the analyzer is adapted for varying the frequency of a variable frequency input signal over a predetermined frequency range to obtain a frequency-dependent resonator response of the mechanical resonator.

Preferably the analyzer is such that the resonator response is then processed to generate a graphical display of the sample being analyzed. It will thus be appreciated that analysis may be performed by comparing sample data output with a reference, with other samples, or both.

By way of example, the resonator of the present invention may be coupled with a network analyzer, such as a Hewlett-Packard 8751A network analyzer, which is adapted for sending a variable frequency input signal to the tuning fork resonator for generating resonator oscillations and for receiving the resonator response at different frequencies.

The resonator output might optionally pass through a suitable high impedance buffer before being measured by a suitable wide band receiver. The invention is not limited to this specific type of network analyzer, however; any other analyzer that generates and monitors the resonator's response over a selected frequency range can be used without departing from the scope of the invention. For example, a sweep generator and AC voltmeter can be used in place of the network analyzer.

Figure 5A:
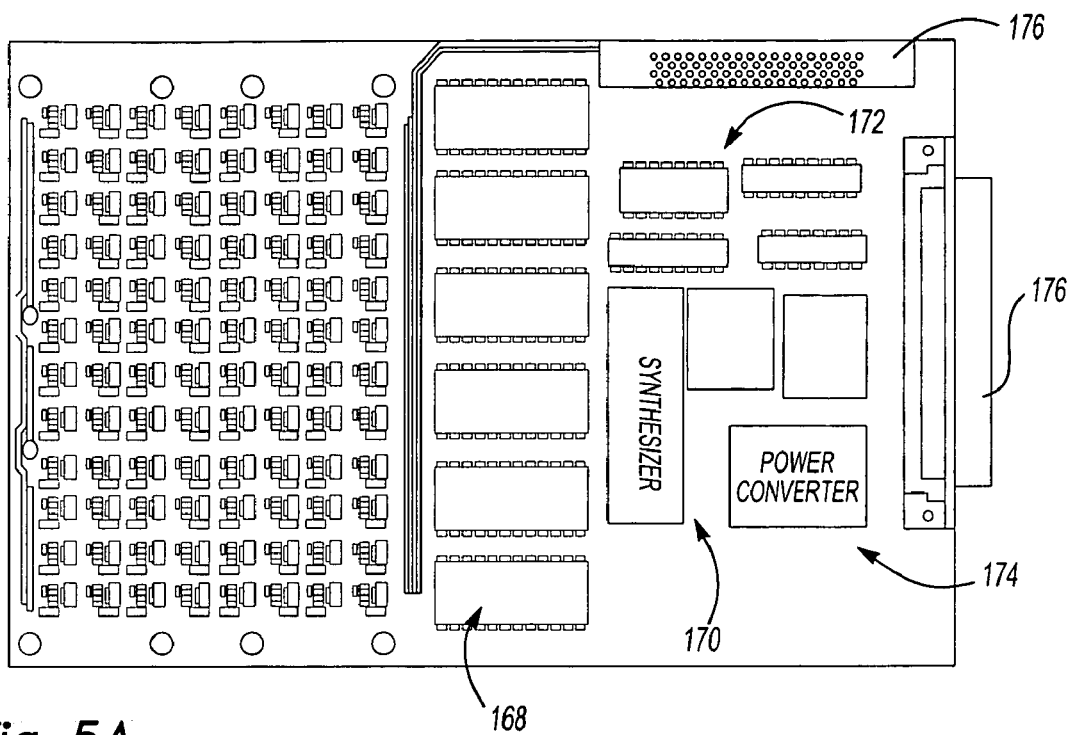
FIG. 5A is a view of illustrative readout electronics for use in connection with the present invention.
Figure 5B:
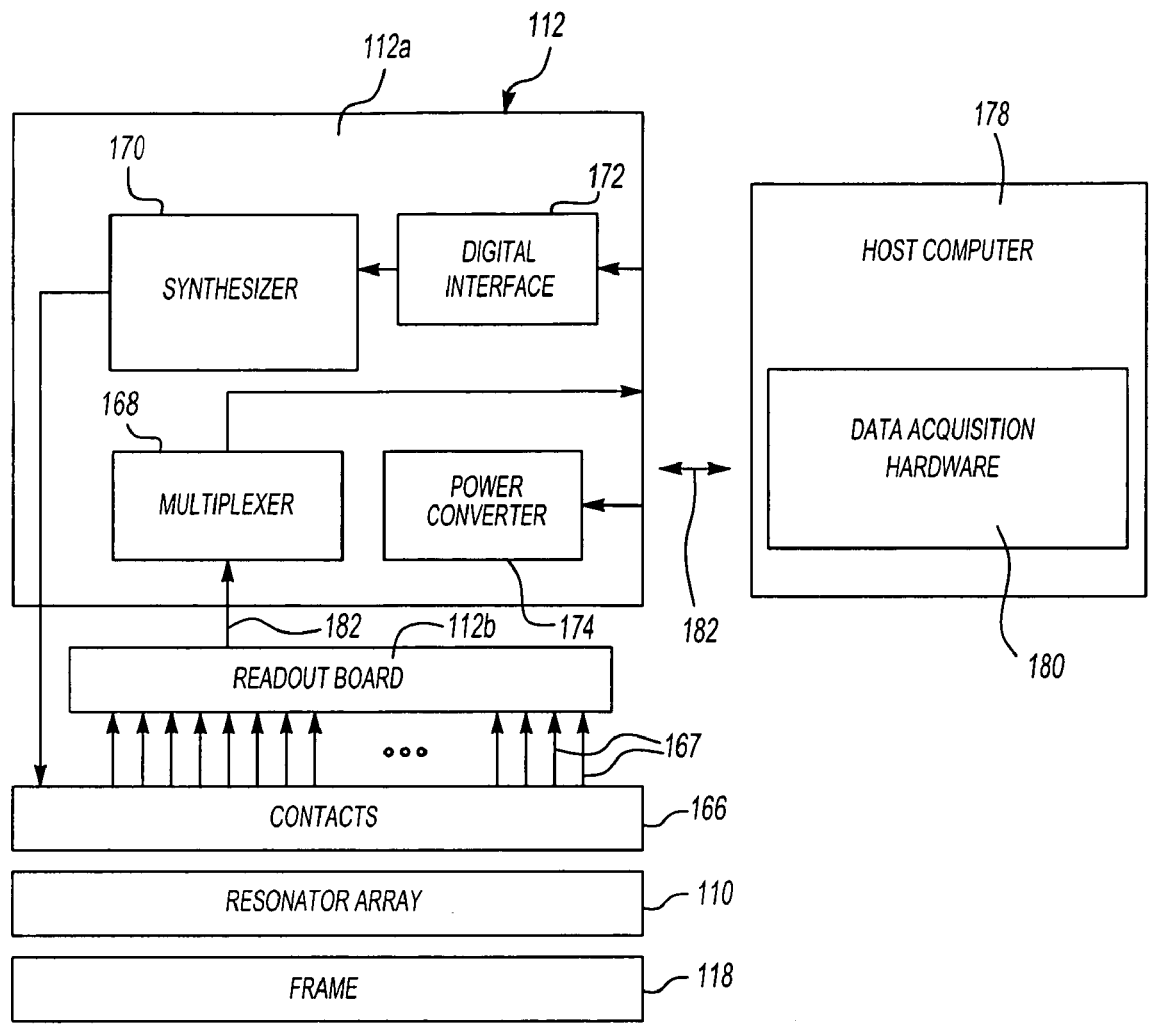
FIG. 5B is a schematic of one preferred electronics assembly of the present invention.

Another approach herein for measurement hardware is to employ a readout board in communication with a computer and any resonators. With reference now to FIGS. 1, 5A and 5B, there are illustrated various approaches to configuring a readout board (preferably readout electronics) for use in connection with the present invention. As can be seen, though one or more hard-wired circuits may be employed, preferably one or a plurality of printed circuit boards are employed to comprise the readout board, thereby affording a compact and reliable structure.

A preferred readout board 112 for a system of the present invention will be one or preferably a plurality of printed circuit boards (e.g., 112a and 112b), one or more of which may include contacts 166 (optionally including a resilient or elastomeric component) for connection with multi-channel (e.g., 8 channels, 96 channels or otherwise) readout electronics (e.g., associated with a second board 112b, such as one that is adapted for placement on a robotic arm) or for electrical communication between the components, such as by using associated plungers or pins 167 (e.g., Pogo® pins). Depending upon the size of the resonator array, where simultaneous measurement is desired, preferably the readout board will include an amount of channels corresponding with at least the number of resonators in the array. The readout board will also be configured to include at least one board 112a that includes or is in signaling communication with a suitable multiplexer component 168 (e.g., an analog multiplexer) for multiplexing. The board 112a is also preferably in signaling communication with or includes a synthesizer component 170 such as a direct digital synthesizer for sine wave synthesis and sweeping of frequency, and is optionally associated with a suitable digital interface component 172 interfacing with a host computer. Optionally, the board 112a may be connected with a suitable power supply (not shown), such as Goodwill Instruments GW3030D. A power converter component 174 may also be employed. As will be appreciated, the readout board may comprise an assembly of plural boards or it may be a single integrated board. In the above manner, a tuning fork array is able to be positioned in a suitable chamber for controlling the environmental conditions.

The system of the present invention is preferably controlled by a suitable controller and more preferably by a host computer 178 such as a desktop, portable or networked personal computer equipped with suitable data acquisition hardware 180. Such hardware is preferably multi-functional and can sustain analog output, digital and counter/timer I/O operations together with their analog input operations. Preferably the hardware will have integrated signal conditioning and will be capable of at least 50 and more preferably at least 100 kS/s sampling rate. The hardware preferably also includes an art-disclosed Real-Time System Integration Bus (RTSI) or PXI Trigger Bus for multiple device synchronization. An example of one preferred type of commercially available data acquisition hardware is that available from National Instruments under the trade designation AT-MIO-16DE-10. The readout board 112 and the computer 178 preferably are connected by one or more cables 182, but other signal transmission means may also be employed.

Figure 5C:
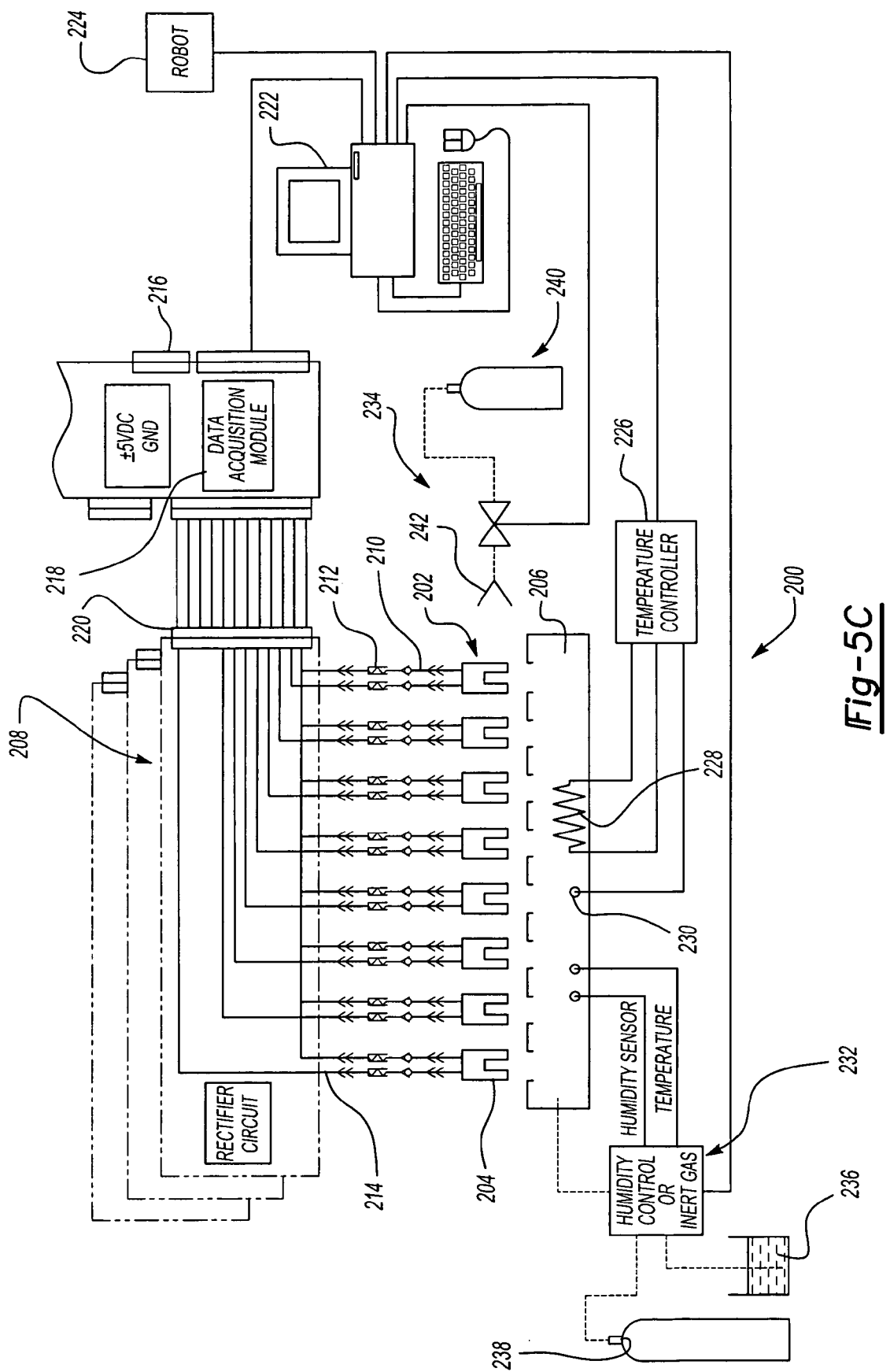
FIG. 5C is a schematic of one preferred system of the present invention.

FIG. 5C illustrates another schematic for a system 200 of the present invention. In this embodiment, a tuning fork array 202 is provided having a plurality of tuning fork resonators 204. A sample chamber 206 is also provided. The tuning fork resonators 204 are assembled in signaling communication with a printed circuit board 208 (e.g., including a rectifier circuit). For example, the tuning fork resonators are connected into one or more first sockets 210 associated with a plunger or pin 212 (e.g., Pogo®-Pins for attachment to a Pogo®-Pin breakout board), in turn being connected by one or more second sockets 214 assembled to the board 208.

The board 208 is connected to a grounded dc power source 216 and data acquisition module 218, with a suitable cable (e.g., 12 cond wire umbilical cable 220). The data acquisition module 218 is connected with a host computer (e.g., PC 222), the latter optionally also being in signaling communication with a robot.

Preferably, the computer 222 also is in signaling communication with one or a combination of a temperature controller 226 for controlling the temperature in the sample chamber 206 (e.g., using a heater 228 and a thermocouple 230 located in the chamber); a humidity control system 232; or a sample gas delivery system 234. The humidity control system preferably controls the moisture level in the chamber 206. Thus, it preferably includes one or more of a moisture supply 236, gas supply 238 (e.g., inert gas supply), and optionally a moisture sensor, temperature sensor or both.

The sample gas delivery system 234 preferably includes a suitably valved gas supply 240 for delivering gas through a nozzle 242 as desired aimed at the samples that are placed upon the resonators, e.g., as a pulse of gas for removing excess sample from the pressure sensitive adhesive to which it is applied prior to testing.

Figure 6:
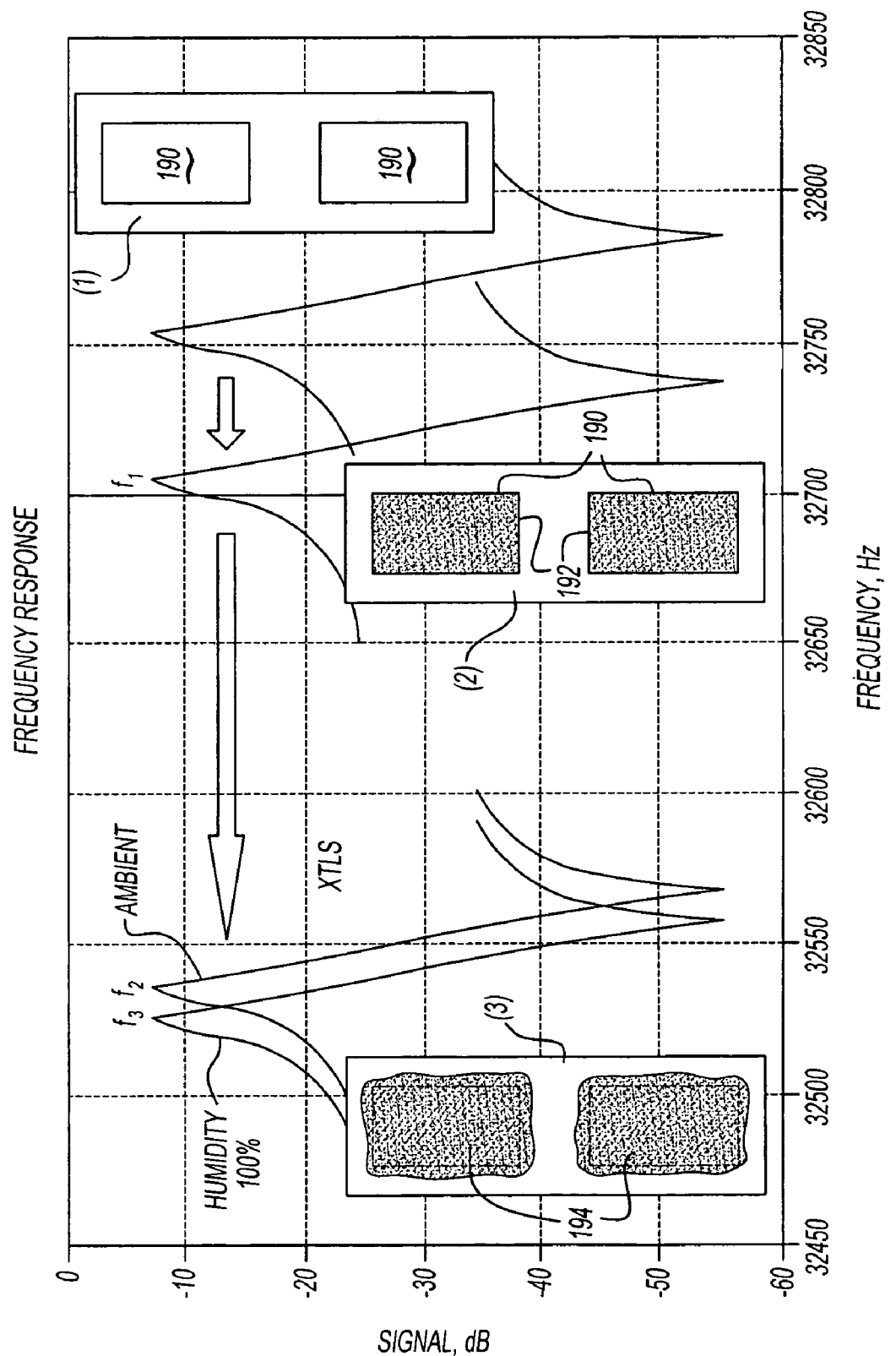
FIG. 6 is a graphical depiction of one illustrative frequency response as one method of the present invention is performed.

Turning now to FIG. 6, the operation of the method and apparatus of the present invention will be described. FIG. 6 schematically illustrates how data could be acquired and analyzed according to one method of the present invention. Superimposed upon the illustrative graphic display of FIG. 6 are three depictions of tips 190 of a two-tine tuning fork at various steps of the method. An early step is illustrated on the far right depiction (1), in which there is shown a tuning fork that is being provided with the tips 190 in a bare condition. As indicated previously, the tuning fork is contacted with a suitable adhesive (e.g., a pressure sensitive adhesive) over some or all of one or both of the tips 190. This can be accomplished in any suitable manner, such as by a manual method of brushing, spraying, dipping, or otherwise coating the tip. It can also be performed automatically, such as with a robot arm having a resonator array attached thereto. The robot arm can bring the tips into contact with an adhesive for applying the coating. The depiction (2) in the center of FIG. 6 illustrates such application of an adhesive 192. It will be appreciated that the inherent tack of some samples may permit for the omission of any adhesive. Thus, adhesive use herein may be optional.

In the far left depiction (3) of FIG. 6, a subsequent step is illustrated pursuant to which sample 194 (shown as the shaded portion) having an initial mass (m) is contacted with the adhesive on the tips 190 and then the sample is subjected to moisture at a desired level (e.g., from 0 to 100% humidity) for changing the mass of the sample ($\Delta m$). It will be appreciated that it is certainly possible to measure larger quantities according to the present invention, but it is especially desirable to employ the present invention for using samples of an initial mass of less than 1 mg, and more preferably less than about 500 µg and even still more preferably less than about 100 µg, or even less than about 10 µg.

The resonator response is measured during all or some these steps, and preferably to determine a frequency response ($f_1$) of the resonator to an applied signal (e.g., before sample is applied, but preferably after any desired adhesive is applied), and intermediate frequency response ($f_2$) of the resonator to the signal (e.g., after the sample is applied, but before subjecting the sample to a moisture), and a frequency response ($f_3$) after subjecting the sample to a varying environmental condition (e.g., after the sample is exposed to moisture). In accordance with the above, in one particularly preferred embodiment, the frequency responses are correlated with mass change of the sample, such as by the equation: $\Delta m/m = (f_2-f_3)/(f_1-f_2)$. It will be appreciated that $\Delta m/m$ could be positive or negative, thus rendering this invention suitable for measuring positive or negative mass changes, such as from sorption, desorption or both. Advantageously, because it involves comparisons, or relative measurements (e.g. measurement of mass with or without water present), such a measurement is not necessarily dependent upon the quantity of the sample, but rather upon observable resonator frequency shifts. Reliable measurements are obtained without the need for meeting a predetermined sample size, thickness or volume threshold requirement.

Further, the use of the present invention permits for the consistent and reproducible rapid acquisition of reliable data. For example, in some instances, where a sample size is less than 1 mg, measurement data is obtained in less than 2 hours, and more preferably less than 1 hour. For very small sample sizes, reliable measurements are obtained in less than 10 minutes, more preferably less than 5 minutes and still more preferably less than 1 minute. Where simultaneous measurements are performed upon a library of samples (e.g., 2 or more samples, 4 or more, 8 or more, 24 or more, 48 or more or even 96 or more sample) the entire library is sampled within the above recited times.

In one aspect of the present invention, the measurements are carried out under a steady state environmental condition (e.g., as to temperature, pressure, moisture level or otherwise). However, the environmental condition may be variable over time as well. For example, without limitation, an environmental condition, such as moisture level, can be ramped up or down, held at constant levels or even be cycled through higher and lower levels.

It is thus contemplated that, where it is impractical to vary a sample condition while the sample is on a resonator, sample measurements may take place within or more suitable chambers within which the environment can be controlled as desired. The chambers may be adapted for receiving the entire measuring system of the present invention or components thereof. For example, it may be preferable to employ an environmental chamber that is capable of receiving and at least partially surrounding the resonator (with sample thereon) or a portion thereof.

A suitable heating or cooling device may be employed as desired in association with any such chamber for controlling temperature within the chamber. The device may be adapted for individually addressing each individual sample alone or a plurality of samples.

Any such chamber may be sealed as desired and one or more gasses introduced therein or removed therefrom for controlling pressure within the chamber.

It will be appreciated that references herein to signaling communication, though illustrated generally in the context of electrical signaling are not intended to be limited thereby.

Other signaling may be employed (e.g., electrical, magnetic, optical, thermal, or other communication).

In one preferred embodiment, the present invention contemplates employing a suitable environmental chamber within which the moisture level can be maintained at one or more predetermined levels, or ramped up or down as desired. In this instance, it is preferable that the chamber be associated with one or more suitable moisture content sources. For example, it may be possible to have an external source that introduces a vapor into the chamber (e.g., a steam source), a source within the chamber that emits a vapor (e.g., a liquid reservoir, a liquid saturated substrate such as a damp sponge, or otherwise), or alternatively a desiccant source (contained or uncontained). Combinations of the above may also be employed.

Figure 7:
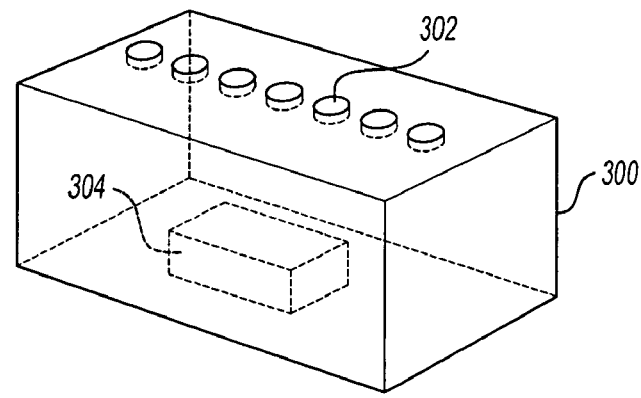
FIG. 7 is a perspective view of one illustrative environmental chamber for use in connection with the present invention.
Figure 8:
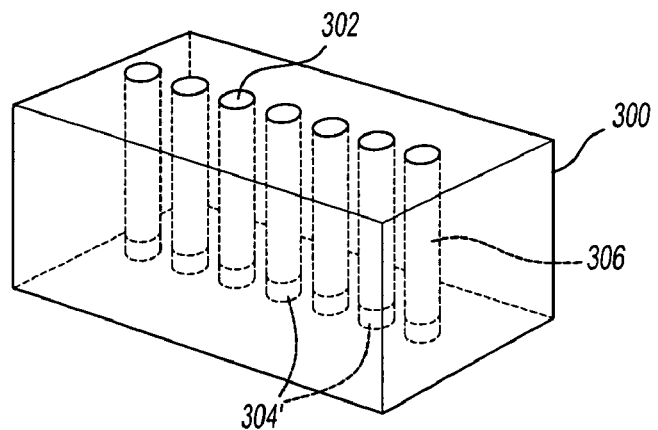
FIG. 8 is a perspective view of an alternative illustrative environmental chamber for use in connection with the present invention.

Referring specifically to FIGS. 7 and 8, there are shown two of the various different approaches to maintaining an environmental condition within a chamber 300, such as the sample chamber 206 of FIG. 5C. Each chamber 300 is shown as an enclosed receptacle, having at least one, and preferably a plurality of openings 302 defined in one of its walls. The chambers may be fabricated as a single integrated structure or as a plurality of structures that are assembled together. The chambers shown in FIGS. 7 and 8 each have at least one moisture content source, preferably located within the chamber. The chambers 300 may be adapted, as in FIG. 7 for subjecting any samples introduced therein to a common moisture content source 304, or as in FIG. 8, to a plurality of moisture content sources 304' (which may provide the same or a different moisture level form source to source within the chamber).

In this regard, one possible construction, shown in FIG. 8 is to have a plurality of wells 306 (e.g., open ended or closed ended tubes) defined within the chamber in fluid communication with the moisture content sources 304'. Of course, a similar structure having wells may also be employed for use with the chamber of FIG. 7.

The structures of FIGS. 7 and 8 can be adapted as desired to regulate the moisture content for one or a plurality of samples. Thus, there can be fewer or greater than the eight openings that are depicted. Further, it is possible that a plurality of chambers are combined in defining a measurement protocol for samples, with certain of the chambers providing a different moisture level or type relative to others.

Referring to FIG. 9, there is seen an illustrative transient response plot for a sample analyzed in accordance with the present invention. Though illustrated by reference to calcium sulfate, similar plots are obtainable using other samples. In general, mass change is plotted as a function of time, upon exposure to the desired environmental condition. Thus, it can be seen that over time, the mass will increase upon exposure to humidity, but decrease upon going from a high humidity condition to a lower one. The slope of the curve and the mass change, of course, may vary also from sample to sample.

Generally, the system of the present invention may include suitable software that can be programmed with information such as synthesis, composition, location information (e.g., with respect to a substrate or substrates) or other information related to a library of samples. The software may be in communication with suitable instrument control software for controlling the preferred analytical instrument of the present invention. The software may also be in communication with data acquisition hardware or software for collecting data from a response from the library samples. Preferably, the instrument control software commands the analytical instrument to expose library members to an oscillating resonator, e.g., in the presence of moisture, in an effort to evoke a response from such library member. At substantially the same time, the instrument monitors the response of the library member and provides data on the response to the data acquisition hardware or software. Thereafter, the instrument control software, the data acquisition hardware or software or both transmit data to the protocol design and execution software such that each library member or information about each library member may be matched with its response and transmitted as data to a suitable database. Once the data is collected in the database, analytical software may be used to analyze the data, and more specifically, to determine properties and characteristics of each library member, or the data may be analyzed manually. Preferably the data is also graphically displayed.

In a preferred embodiment, the system of the present invention is driven by suitable software for designing the library, controlling the instruments for mechanical property screening, and data acquisition, viewing and searching, such as LIBRARY STUDIO®, by Symyx Technologies, Inc. (Santa Clara, Calif.); IMPRESSIONIST™, by Symyx Technologies, Inc. (Santa Clara, Calif.); EPOCH™, by Symyx Technologies, Inc. (Santa Clara, Calif.); or a combination thereof. The skilled artisan will appreciate that the above-listed software can be adapted for use in the present invention, taking into account the disclosures set forth in commonly-owned and copending U.S. patent application Ser. No. 09/174,856, filed on Oct. 19, 1998, U.S. patent application Ser. No. 09/305,830, now granted as U.S. Pat. No. 6,507,945 filed on May 5, 1999 and PCT Application No. PCT/US00/12228, published as WO 00/67086, U.S. patent application Ser. No. 09/420,334, filed on Oct. 18, 1999, U.S. application Ser. No. 09/550,549, filed on Apr. 14, 2000, each of which is hereby incorporated by reference. Additionally, the system may also used a database system developed by Symyx Technologies, Inc. to store and retrieve data with the overlays such as those disclosed in commonly-owned and copending U.S. patent application Ser. No. 09/755,623, now issued as U.S. Pat. No. 6,658,429 filed on Jan. 5, 2001, which is hereby incorporated by reference for all purposes. The software preferably provides graphical user interfaces to permit users to design libraries of materials by permitting the input of data concerning the precise location on a substrate of a material (i.e., the address of the material). Upon entry, the software will execute commands for controlling activity at such individual address.

It will be appreciated that, because the properties of materials can depend on environmental conditions—temperature, pressure, ambient gas composition (including humidity), electric and magnetic field strength, and so on—the screening instruments discussed above may include a control system for regulating environmental condition. Useful systems may include an environmental chamber (e.g., as illustrated in FIGS. 7 and 8) that encloses the samples (e.g., before or during analysis). The system may also use computer software to regulate conditions in the environmental chamber.

In another embodiment of the present invention, there is contemplated that there will be sample handling involved in order to transfer a synthesized sample from a substrate to a mechanical resonator for analysis. Suitable manual or automated handling equipment may be employed as desired. In one embodiment, handling may be done using a microprocessor controlling an automated system (e.g., a robot arm). Preferably, the microprocessor is user-programmable to accommodate libraries of samples having varying arrangements of samples (e.g., square arrays with "n-rows" by "n-columns", rectangular arrays with "n-rows" by "m-columns", round arrays, triangular arrays with "r-" by "r-" by "r-"equilateral sides, triangular arrays with "r-base" by "s-" by "s-"isosceles sides, etc., where n, m, r, and s are integers).

The present invention may be employed by itself or in combination with other screening protocols for sample analysis. For example, it is contemplated that the present invention involves measuring hygroscopicity of a sample in combination with at least one other characterization step, such as X-ray analysis, chromatography, mass spectrometry, optical screening, infrared screening, electrochemical screening, or the like.

Without limitation, examples of other screening techniques, which might be combined with the analysis of the present invention, include those addressed in commonly-owned U.S. Pat. No. 6,371,640 (Hajduk, et al); U.S. Pat. No. 6,182,499 (McFarland, et al); U.S. Pat. No. 6,175,409 B1 (Nielsen, et al); U.S. Pat. No. 6,157,449 (Hajduk, et al ); U.S. Pat. No.6,151,123 (Nielsen); U.S. Pat. No. 6,034,775 (McFarland, et al); U.S. Pat. No. 5,959,297 (Weinberg, et al); U.S. Pat. No. 5,776,359 (Schultz et al), commonly owned and copending U.S. patent application Ser. No. 09/580,024, now granted as U.S. Pat. No. 6,664,067, titled "Instrument for High Throughput Measurement of Material Physical Properties and Method of Using Same," filed on May 26, 2000, all of which are hereby expressly incorporated by reference herein.

As indicated previously, the present invention preferably employs a resonator array for measuring a plurality of samples applied to the resonator as part of a combinatorial research program. The invention may also be employed, particularly where a single tuning fork resonator or a tuning fork resonator array is employed in the absence of an applied sample, such as for measuring ambient moisture levels, the presence or absence of a particular biological or gaseous species, or otherwise.

Another useful application of the present invention is for the performance of thermogravimetric analysis (TGA), such as to measure desorption of water or solvent vapor as a function of temperature, decomposition, reaction kinetics or the like. Pursuant to such analysis, a sample is provided to a resonator element as described herein. The sample is heated for changing the mass of the sample. The response of the resonator to the change of mass is monitored. An individual resonator element can be employed for measuring one sample at a time, as may be an array of resonator elements for simultaneous measurement of a plurality of samples.

Yet another useful application of the present invention is for the rapid measurement of mass change resulting from corrosion or oxidation. Pursuant to such analysis, a sample is provided to a resonator element as described herein. The sample is exposed to an oxidative or corrosive media for changing the mass of the sample. The response of the resonator to the change of mass is monitored. An individual resonator element can be employed for measuring one sample at a time, as may be an array of resonator elements for simultaneous measurement of a plurality of samples.

It should also be appreciated that monitoring of response of a resonator herein may involve a self-oscillatory mode, pursuant to which the step typically need only involve monitoring frequency of the circuit output voltage.

Unless stated otherwise, dimensions and geometries of the various structures depicted herein are not intended to be restrictive of the invention, and other dimensions or geometries are possible. Plural structural components step can be provided by a single integrated structure or step. Alternatively, a single integrated structure step might be divided into separate plural components or steps. By way of example, without limitation, it is possible that a resonator is driven by a first actuation mechanism and its resulting vibration measured by a separate detector. However, it is also possible that the functions of actuation and detection are integrated into a single device.

In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

What is claimed is:

1. A method for controlling a process including polymer particulate, the method comprising contacting a mechanical resonator with polymer particulate in a chamber enclosing the polymer particulate, the mechanical resonator being a flexural resonator and being contacted with the polymer particulate in the presence of a flow of gas in the chamber, controlling one or more environmental conditions of the chamber, measuring the mass or mass change of the polymer particulate at a first time by applying an input signal to the mechanical resonator, monitoring a response of the mechanical resonator to the input signal, the response being represented by a response signal of the mechanical resonator, and processing the response signal to determine the mass or the mass change of the polymer particulate at the first time, varying one or more of the controlled environmental conditions in the chamber after the first time, and measuring the mass or mass change of the polymer particulate at a second time after varying the one or more of the controlled environmental conditions by applying an input signal to the mechanical resonator, monitoring a response of the mechanical resonator to the input signal, the response being represented by a response signal of the mechanical resonator, and processing the response signal to determine the mass or the mass change of the polymer particulate at the second time.

2. The method of claim 1 wherein the mass or mass change of the polymer is measured over time.

3. The method of claim 1 wherein the mechanical resonator is contacted with polymer in the presence of a flow of gas in the chamber.

4. The method of claim 1 wherein the polymer is a polymer particulate.

5. The method of claim 1 wherein the polymer is an irregularly-shaped polymer particulate.

6. The method of claim 1 wherein the polymer is a polymer blend.

7. The method of claim 1 wherein the chamber encloses the polymer.

8. The method of claim 1 wherein the temperature of the chamber is controlled.

9. The method of claim 1 wherein the pressure of the chamber is controlled.

10. The method of claim 1 wherein the temperature and the pressure of the chamber are controlled.

11. The method of claim 1 wherein the polymer is monitored at the first time and the second time to measure the mass or mass change of the polymer at the first time and the second time, by a method comprising actuating the mechanical resonator, monitoring a response of the actuated mechanical resonator, and correlating the monitored response to the mass or the mass change of the polymer.

12. The method of claim 11 wherein the mechanical resonator is actuated by applying an input signal to the mechanical resonator.

13. The method of claim 1 wherein the polymer is monitored at the first time and at the second time by a method comprising
    applying an input signal to the mechanical resonator,
    monitoring a response of the mechanical resonator to the input signal, the response being represented by a response signal of the mechanical resonator, and
    processing the response signal to determine the mass or the mass change of the polymer.

14. The method of claim 1 wherein the mass or mass change of the polymer is measured in less than one minute.

15. The method of claim 1 wherein the polymer is monitored at the first time in less than one minute and the polymer is monitored at the second time in less than one minute.

16. The method of claims 1 or 11 wherein the mass or mass change of the polymer is measured at the first time in less than one minute and the mass or mass change of the polymer is measured at the second time in less than one minute.

17. The method of claims 1 or 11 wherein the mass or mass change of the polymer is measured by a method comprising
    applying an input signal to the mechanical resonator,
    monitoring a response of the mechanical resonator to the input signal, the response being represented by a response signal of the mechanical resonator, and
    processing the response signal to determine the mass or the mass change of the polymer.

18. The method of claims 1 or 11 wherein the mass or mass change of the polymer is measured by a method comprising
    applying a variable frequency input signal to the mechanical resonator,
    varying the frequency of the variable frequency input signal over a predetermined frequency range,
    obtaining a frequency-dependent response of the mechanical resonator to the input signal, the response being represented by a response signal of the mechanical resonator, and
    processing the response signal to determine the mass or the mass change of the polymer.

19. The method of claim 1 wherein the mechanical resonator is a tuning fork resonator.

20. The method of claim 1 wherein the mechanical resonator is a piezoelectric resonator.

21. The method of claim 1 wherein the mechanical resonator is a flexural resonator, and the flexural resonator is actuated by applying an input signal having a frequency of less than about 1 MHz.

22. The method of claim 1 wherein the mechanical resonator is a flexural piezoelectric resonator, and the flexural piezoelectric resonator is actuated by applying an input signal having a frequency of less than about 500 kHz.

23. The method of claims 1 or 11 wherein the mass or mass change of the polymer is measured using measurement hardware comprising a plurality of mechanical resonators in an array, each of the plurality of mechanical resonators being adapted for contacting polymer in the chamber.

24. The method of claims 1 or 11 wherein the mass or mass change of the polymer is measured using measurement hardware comprising a plurality of mechanical resonators in an array, each of the plurality of mechanical resonators being adapted for contacting polymer in the chamber, and using software for controlling the measurement hardware, the software being programmed with location information for the plurality of mechanical resonators.

* * * * *